(12) United States Patent
Olovsson et al.

(10) Patent No.: US 11,571,635 B2
(45) Date of Patent: Feb. 7, 2023

(54) LIQUID CHROMATOGRAPHY SYSTEM, A DEVICE, AND A METHOD

(71) Applicant: Cytiva Sweden AB, Uppsala (SE)

(72) Inventors: Bjorn Markus Olovsson, Uppsala (SE); Anders Ljunglof, Uppsala (SE); Karol Maciej Lacki, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 444 days.

(21) Appl. No.: 15/562,586

(22) PCT Filed: Mar. 23, 2016

(86) PCT No.: PCT/EP2016/056407
§ 371 (c)(1),
(2) Date: Sep. 28, 2017

(87) PCT Pub. No.: WO2016/156153
PCT Pub. Date: Oct. 6, 2016

(65) Prior Publication Data
US 2018/0111059 A1    Apr. 26, 2018

(30) Foreign Application Priority Data
Mar. 31, 2015 (GB) ..................................... 1505519

(51) Int. Cl.
*B01D 15/00* (2006.01)
*B01D 15/38* (2006.01)
(Continued)

(52) U.S. Cl.
CPC ......... *B01D 15/1864* (2013.01); *B01D 15/14* (2013.01); *B01D 15/1807* (2013.01);
(Continued)

(58) Field of Classification Search
CPC ................ B01D 15/14; B01D 15/3809; B01D 15/1864; B01D 15/1807; C12N 7/00;
(Continued)

(56) References Cited

U.S. PATENT DOCUMENTS 4,389,316 A    6/1983   Falk
2006/0240511 A1*  10/2006  Eskling .................. C07K 14/71
                                                           435/69.1
(Continued)

FOREIGN PATENT DOCUMENTS

EP           2578286 A1     4/2013
WO      2013/180647 A1    12/2013

OTHER PUBLICATIONS

PCT International Search Report and Written Opinion for PCT Application No. PCT/EP2016/056407 dated Aug. 18, 2016 (15 pages).
(Continued)

*Primary Examiner* — Rebecca M Fritchman
(74) *Attorney, Agent, or Firm* — Eversheds Sutherland (US) LLP

(57) ABSTRACT

The present invention relates to a liquid chromatography system for the separation of bio-molecules in a fluid including at least two unit operations, wherein the first unit operation is a step of multi-column chromatography and the second unit operation is a step modifying said bio-molecules and/or the fluid, wherein the modification comprises feeding the fluid resulting from the last chromatography column of the first unit operation into a system comprising at least two containers, wherein each container has a volume and a moveable sidewall arranged to divide the volume into a first sub-volume and a second sub-volume, and each container comprises a first port connected to the first volume and a second port connected to the second sub-volume. The invention also relates to a virus inactivation device for a chroma-
(Continued)

tography system according to the invention, which enables continuous or semi-continuous processing of biomolecules, as well as a method of using such a device.

15 Claims, 3 Drawing Sheets

(51) Int. Cl.
*B01D 15/18* (2006.01)
*B01D 15/14* (2006.01)
*G01N 30/46* (2006.01)
*C07K 1/22* (2006.01)
*C12N 7/00* (2006.01)
*G01N 30/20* (2006.01)
*G01N 30/88* (2006.01)

(52) U.S. Cl.
CPC ............ *B01D 15/3809* (2013.01); *C07K 1/22* (2013.01); *C12N 7/00* (2013.01); *G01N 30/465* (2013.01); *G01N 2030/208* (2013.01); *G01N 2030/8813* (2013.01)

(58) Field of Classification Search
CPC ..... G01N 2030/208; G01N 2030/8813; G01N 30/465; C07K 1/22
See application file for complete search history.

(56) References Cited

U.S. PATENT DOCUMENTS

2014/0251913 A1* 9/2014 Lacki ................. B01D 15/1871
 210/659
2014/0255994 A1* 9/2014 Konstantinov .... B01D 15/3814
 435/69.6

OTHER PUBLICATIONS

GB Search Report for GB Application No. 1505519.7 dated Nov. 27, 2015 (3 pages).
GB Search Report for GB Application No. 1510539.8 dated Dec. 4, 2015 (3 pages).
GE Healthcare: "Data File 18-1134-31 AC; Liquid Chromatography; Superloop 10 ml, 50 ml, 150 ml," 2007, XP002758793; https://www.gelifesciences.com/gehclsimages/GELS/Related%20Content/Files/1314716762536/itdoc18113431AC_20110830173308.pdf (4 pages).
Japanese Office Action for JP Application No. 2017-550923 dated Feb. 3, 2020 (8 pages with English translation).
European Office Action for EP Application No. 16711307.5 dated Mar. 26, 2021 (10 pages).

* cited by examiner

LIQUID CHROMATOGRAPHY SYSTEM, A DEVICE, AND A METHOD

CROSS REFERENCE TO RELATED APPLICATIONS

This application claims the priority benefit of PCT/EP2016/056407 filed on Mar. 23, 2016 which claims priority benefit of Great Britain Application Nos. 1505519.7 and 1510539.8 filed Mar. 31, 2015 and Jun. 16, 2015, respectively. The entire contents of which are hereby incorporated by reference herein.

TECHNICAL FIELD

The present invention relates to liquid chromatography, and more specifically to a system for the separation of biomolecules in a fluid, a device enabling the processing of said biomolecules and/or fluid and a method of using a device according to the invention.

BACKGROUND

Liquid chromatography is one of the most commonly used separation principles in the analysis and manufacture of biomolecules, such as proteins and peptides. There are numerous commercial instruments available for the processing of biomolecules by chromatography today, most of which enable automated processing. However, most liquid chromatography systems require some manual intervention, such as sample application, change of operating parameters etc. which may make their use time-consuming and more labour-intensive than desired.

In order to speed up the processing of biomolecules, development is also moving towards continuous processing when possible. One method which is increasingly used for rapid separation of biomolecules from complex fluids such as fermentation liquids is multiple column chromatography, such as periodic counter current chromatography (pcc). As is well known to the skilled person in this field, multi-column chromatography consists of several chromatographic columns which may be switched in position opposite to the flow direction. Columns may be equipped with pumps, and fluid streams are internally recycled to optimise the performance. Systems may be split into several sections, from which every section performs a task analog to the tasks of a batch purification.

As is also well known to the skilled person, in addition to the separation of biomolecules, the processing thereof will normally include further steps upstream and downstream of the chromatography column. Examples of upstream processing are for example the lysis of cells originating from a culturing process and filtration to remove cell debris and the like. Other processing that may take place upstream or downstream may include either modification of the actual biomolecule, such as modification of the glycosylation of a protein and polymer modification, such as PEGylation; or modification of the fluid wherein the biomolecule is present. The simpler modification of the fluid would include pH change and/or salt additions, while a more complex and currently more time-consuming process is virus-inactivation.

Virus-inactivation of a fluid comprising biomolecules is most commonly performed by addition of the appropriate chemicals, which requires a certain period of time for sufficient inactivation to take place. Including virus-inactivation, as well as other modifications of biomolecules and/or fluid in a continuous process presents a challenge in terms of suitable equipment as well as methodology. There is still a need in analytical as well as preparative scale chromatography for improved systems which enable automated and continuous processing of biomolecules.

SUMMARY

The above stated object is achieved by means of a virus inactivation device, a method, and a system.

A first aspect of the present invention is defined in claim 1. A second aspect of the present invention is defined in claim 7.

A third aspect of the present invention is defined in claim 12.

Other embodiments and advantages of the present invention will appear from the dependent claims and the detailed description that follows.

DETAILED DESCRIPTION

Figure 1:
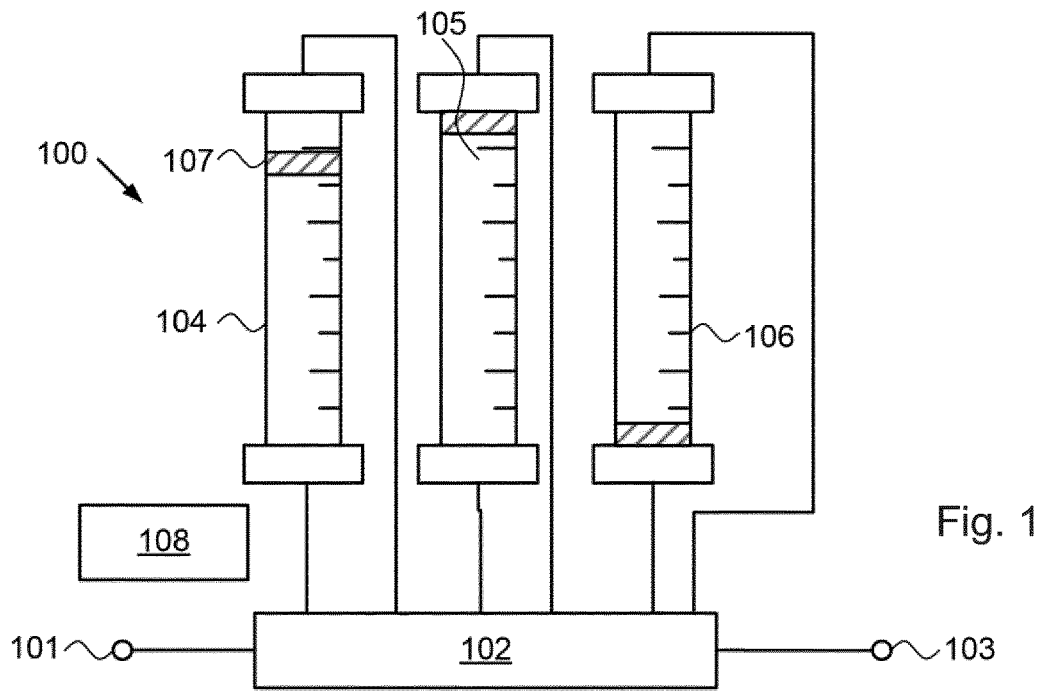
FIG. 1 is a schematic drawing of a virus inactivation device according to one embodiment of the present invention.

The embodiments of this disclosure will now be described more fully hereinafter with reference to the accompanying drawings, in which different example embodiments are shown. These example embodiments are provided so that this disclosure will be thorough and complete and not for purposes of limitation. In the drawings, like reference signs refer to like elements.

A first aspect of the present invention is a liquid chromatography system for the separation of bio-molecules in a fluid including at least two unit operations. The first unit operation is a step of multi-column chromatography, and the second unit operation is a step of modifying said bio-molecules and/or the fluid. In the second unit operation, the modification comprises feeding the fluid resulting from the last chromatography column of the first unit operation into a system comprising at least two containers (104,105,106), wherein each container has a volume and a moveable sidewall (107) arranged to divide the volume into a first sub-volume and a second sub-volume, and each container comprises a first port connected to the first volume and a second port connected to the second port.

The system according to the invention can be used to design a continuous process for the processing of any biomolecule. In an advantageous embodiment, such a system is fully, or to a large extent, automated.

More specifically, the first unit operation may be a multi-column column pcc (periodic counter current chromatography) system, preferably a 4 pcc system, which includes packed bed chromatography columns.

In an advantageous embodiment, the chromatography columns of the first unit operation are packed with a media selected from the group consisting of affinity chromatography media, such as Protein A media or Protein L media; ion exchange media, such as cation or anion exchange media; hydrophobic interaction chromatography media; reverse phase chromatography media; and multi modal chromatography media. Such media and other suitable for use in the present invention are commercially available and well known to the skilled person in this field.

In one embodiment, the second unit operation is arranged to provide for maintenance of biomolecules present in the fluid resulting from the last chromatography column for a pre-determined period of time. This will enable the modification of the biomolecule and/or fluid in any way suitable or required in a process for the separation of such biomolecule in a less manual and advantageously quicker way that possible using conventional technology.

The second unit operation may be performed according to the invention as a step included before the polishing step of an established bioprocess. In an alternative embodiment, the second unit operation is performed after the polishing step. In a specific embodiment, the second unit operation is performed as integrated with the polishing step, using e.g. reverse phase chromatography In an illustrative embodiment of the system according to the invention, the second unit operation provides for a modification selected from the group consisting of inactivation of virus, proteases and/or endoglycanases; modification of the biomolecule by adding a group, such as a polymer, e.g. PEG; and modification of the biomolecule by removing a group. Virus inactivation in chromatography is well known, see e.g. Sofer G (2003) Virus inactivation in the 1990s—and into the $21^{st}$ century, Biopharm International 16, 50-57.

In a specific embodiment, the present invention relates to a system as described in the present application, wherein the biomolecule is an antibody, such as a monoclonal antibody or a fusion or fragment thereof; the first unit operation comprises a first chromatography column packed with Protein A media; and the second unit operation provides for virus inactivation. The virus inactivation is advantageously performed at low pH, such as 3-4. The maintenance time in the container i.e. the incubation at low pH may last for 5-60 minutes, depending on the exact pH, the temperature, the expected presence of virus etc. In a specific embodiment, the parameters for virus-inactivation are set to satisfy the regulatory requirements of a bioprocess for the manufacture of a biological drug.

In an illustrative embodiment, the present invention relates to continuous virus inactivation by the parallel use of two containers as described above, sometimes denoted "super-loops". As the skilled person will appreciate, this embodiment may by varied to include two or three parallel containers according to the invention, adapted for different scales by varying the diameters and heights thereof.

A second aspect of the present invention relates to a device which may be used as described above.

FIG. 1 shows a virus inactivation device, generally designated 100, according to one embodiment of the invention. The virus inactivation device has an inlet port 101 configured to be connected to a chromatography system. The inlet port 101 is connected to a flow controller 102. The flow controller 102 is further connected to an outlet port 103. The virus inactivation device further comprises a group of containers 104,105,106.

Each of the containers in the group of containers 104, 105,106 has a volume and a moveable sidewall 107 arranged to divide the volume into a first sub-volume and a second sub-volume. Each container comprises a first port connected to the first volume and a second port connected to the second sub-volume. The first and the second port of each container are connected to the fluid controller 102.

The fluid controller 102 is configured to select a container from the group of containers that is empty or has been in a filled state during a time equal to or longer than the virus inactivation time.

The fluid controller 102 is further configured to direct the fluid flow from the inlet port 101 to a port of an empty sub-volume of the selected container in the group of containers.

When the sub-volume of the selected container is filled, the flow is directed to another empty sub-volume of another container in the group, which another container is empty or has been in a filled state during a time equal to, or longer than, the virus inactivation time.

The fluid pressure resulting from filling of the empty sub-volume acts on the moveable sidewall 107 and so causes the filled sub-volume to flow its contents to the outlet port via its respective first or second port. Hence, by filling an empty sub-volume the filled sub-volume is emptied by means of the moveable sidewall 107 acting as a piston.

Figure 2:
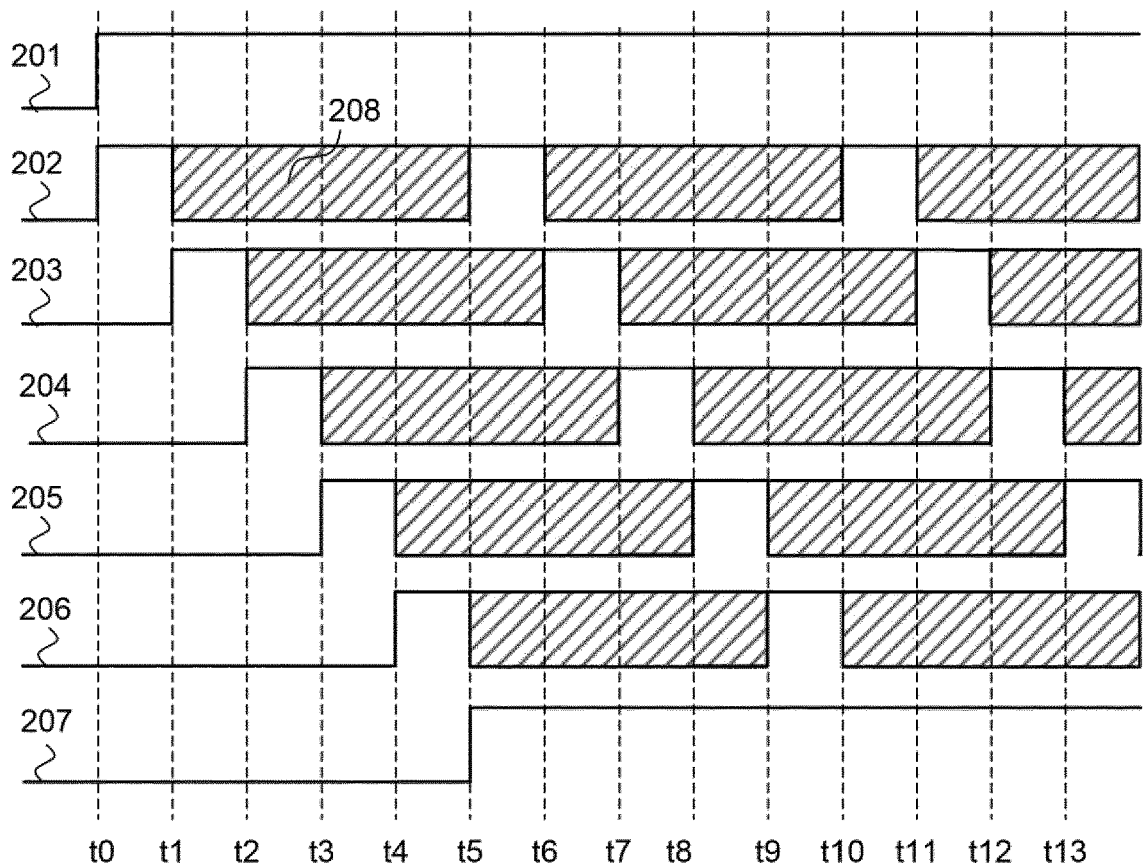
FIG. 2 is a plot of the flows in the virus inactivation device according to one embodiment of the invention with two containers.

FIG. 2 illustrates the operation of a virus inactivation device according to the invention as a plot of flows in the device, the flow received by the virus inactivation device is illustrated as curve 201, at time t0 the operation of the virus inactivation device is initiated and a constant inflow is received after time t0. The flow controller 102 directs the inlet flow to a first container illustrated in curve 202. At time t1 the first container is filled and a sub-sequent virus inactivation is performed by means of UV light, pH adjustments etc. The inlet flow at t1 is then directed to a second container illustrated as curve 203. Gradually, a third to a fifth container is filled one at a time at times t2, t3 and t4 illustrated in curves 204,205,206. At time t5 the virus inactivation in the first container is ready and by directing the inlet flow to the empty sub-volume of the first reservoir, the filled sub-volume of the first container will be emptied to the outlet port by means of the moveable wall. This sequence is repeated for each container in the group and after the first virus inactivation time from t1 to t5 a constant virus inactivated flow from the outlet port will be provided, illustrated in curve 207 after t5.

Figure 3:
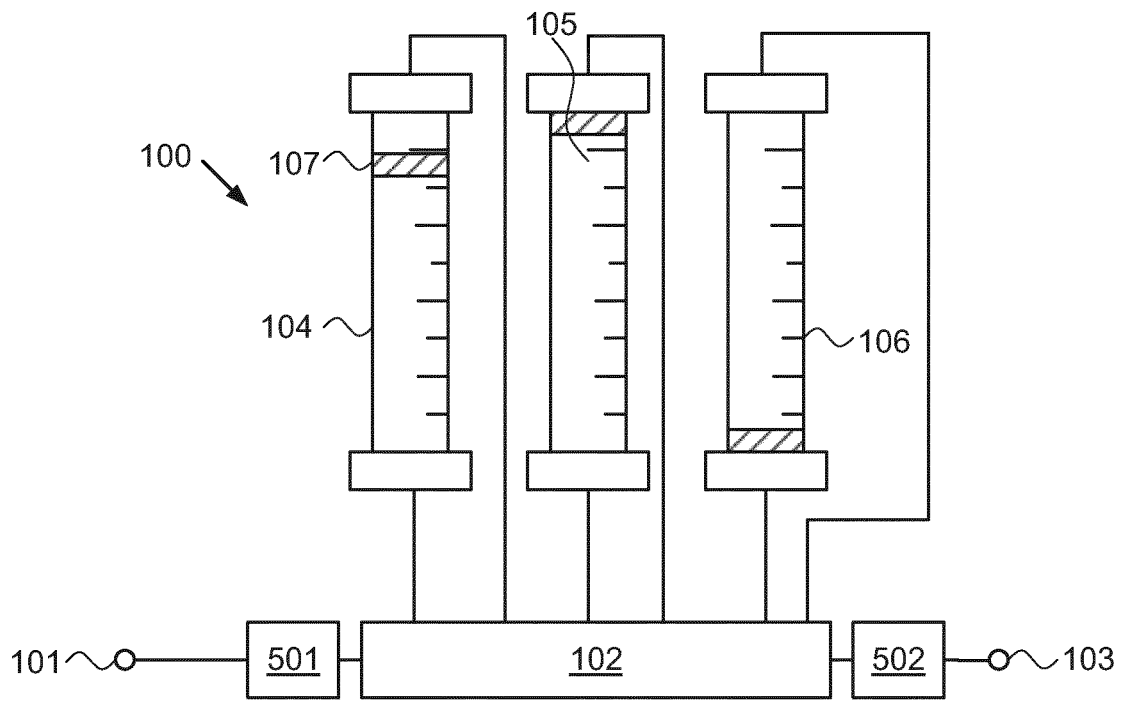
FIG. 3 is a schematic drawing of a virus inactivation device according to one embodiment of the present invention.

FIG. 3 illustrates one embodiment wherein the virus inactivation is performed by lowering the pH at the inlet 101 by means of a pH adjustment device 501. After a predetermined virus inactivation time the pH is raised by means of a second pH adjustment device 502. This embodiment assures that all parts of the fluid flow are subjected to a necessary pH lowering for a predetermined virus inactivation time.

Figure 4:
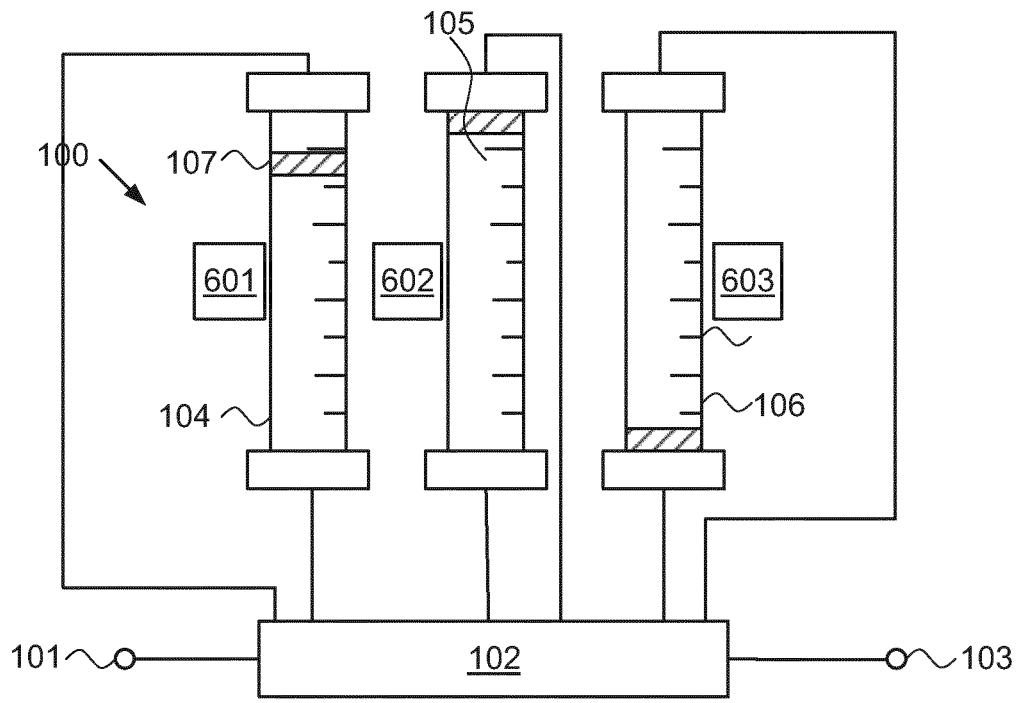
FIG. 4 is a schematic drawing of a virus inactivation device according to one embodiment of the present invention.

Another embodiment is disclosed in FIG. 4 This embodiment uses dedicated UV light sources 601, 602, and 603 configured to illuminate and irradiate respectively each of the containers 104,105 and 106 for the predetermined virus inactivation time.

In order to dimension the virus inactivation device an equation was derived for the number of containers N:

$$N = T \times f / V + 1 \qquad \text{eq1}$$

where T is the predetermined virus inactivation time including an allowance of time for washing the container and raising and lowering the pH, V is the volume of each container in the group, and f is the inlet flow to be virus in-activated.

A third aspect of the present invention relates to a method for a virus inactivation device as set out above.

Figure 5:
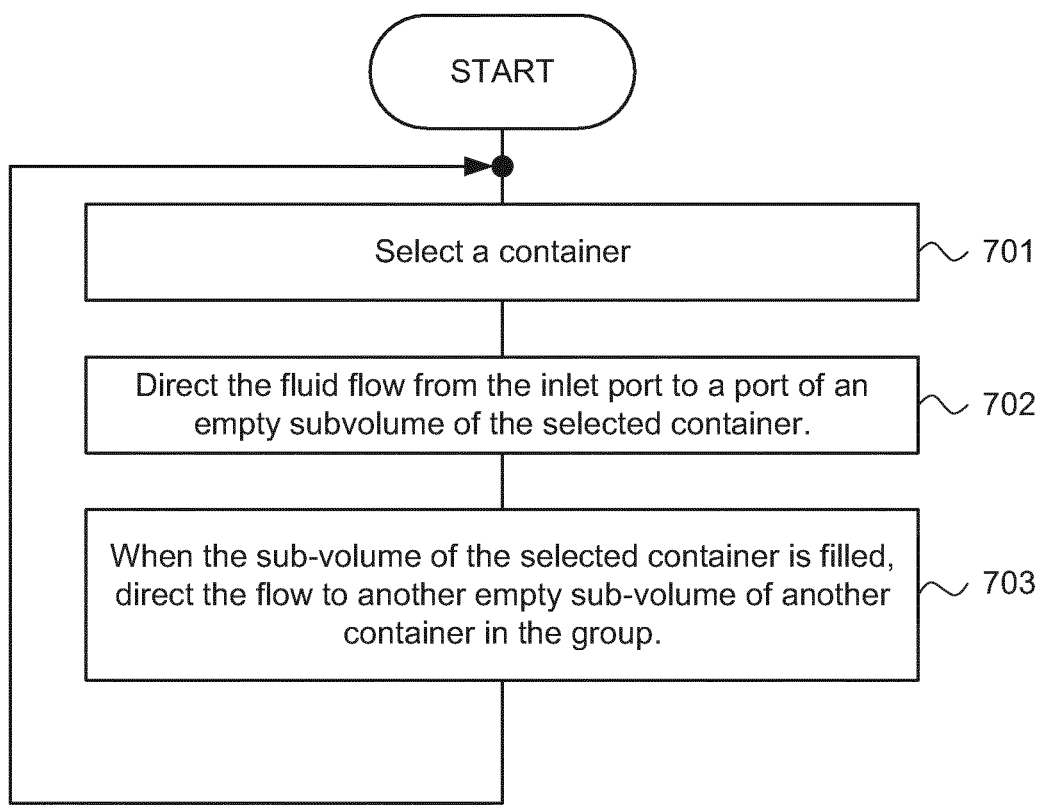
FIG. 5 is a flowchart illustrating a method for a virus inactivation device according to one embodiment of the present invention.

FIG. 5 illustrates a method for virus inactivation according to the present invention as a flowchart. The first step 701 involves selecting a container that is empty or has been in a filled state during a time equal to or longer than the virus inactivation time.

The second step 702 involves directing the fluid flow from the inlet port to a port of an empty sub-volume of the selected container in the group.

A third step 703 involves determining when the sub-volume of the selected container has been filled, directing the flow to another empty sub-volume of another container in the group, which container is empty or has been in a filled state during a time equal to or longer than the virus inactivation time.

The filling of the empty sub-volume causes the filled sub-volume to flow its content to the outlet port by means of the moveable sidewall (107).

In one embodiment of the invention may the container be a super-loop as set out in U.S. Pat. No. 4,389,316 A.

EXPERIMENTAL PART

The present examples are provided for illustrative purposes only, and should not be construed as limiting the examples as defined by the appended claims. All references provided below and elsewhere in the present specification are hereby included herein via reference.

Example 1—Continuous Inactivation of Virus in Mab Processing Using Two Containers (Superloops)

A feed comprised of fluid comprising monoclonal antibody (Mab) is received from a continuous cell culturing process and captured by affinity chromatography using Protein A media (MabSelect®, available from GE Healthcare online) in accordance with well known techniques.

The virus-inactivation is included into a continuous process in accordance with the present invention by providing two containers as described herein, also known as superloops, in parallel. Each superloop is equipped with a two way movable seal, allowing fluid to be applied and eluted both from the top and bottom of the loop. Fluid pH-adjusted MAb feed (pH 3.5) resulting from the chromatography column is applied to a first loop (loop 1). When loop 1 is filled with fluid to a satisfactory level, it is maintained in the container for 30 minutes, while the MAb feed resulting from the chromatography column is shifted and applied to a second loop (loop 2). When loop 2 is filled to a satisfactory level, new MAb feed is applied to loop 1 using opposite flow direction (while MAb in loop 2 is allowed to stand). At the same time the virus inactivated MAb in loop 1 is eluted and can be applied to the next purification column.

This example shows how two parallel "two way containers/superloops" can be used with a protocol of applying new MAb feed—allow to stand—apply new MAb feed in opposite direction and at the same time elute the virus inactivated MAb to obtain a continuous virus inactivation procedure within Mab processing.

The invention claimed is:

1. A liquid chromatography system for the separation of bio-molecules in a fluid comprising:
    a multi-column chromatography (MCC) arrangement comprising a plurality of columns connected in series, each column of the plurality of columns containing media therein for the separation of said bio-molecules, the plurality of columns including at least a first column and a last column;
    at least two containers for processing said bio-molecules, wherein the last column is connected to each of the at least two containers so that fluid output from the last column is fed into each of the at least two containers, wherein the bio-molecules first flow through the first column, wherein at least one of the at least two containers comprises a virus inactivation means; and
    a controller connected to the virus inactivation means,
    wherein each container has a volume and a moveable sidewall arranged to divide the volume into a first sub-volume and a second sub-volume,
    wherein each container comprises a first port connected to the first sub-volume and a second port connected to the second sub-volume,
    wherein the controller is configured to successively direct a flow of the fluid for exposure to the virus inactivation means to a respective container of the at least two containers that is empty or has been in a filled state during a time equal to or longer than the virus inactivation time to continuously inactivate a virus in the fluid, and
    wherein the moveable sidewall of each container is moveable (i) in response to fluid pressure resulting from filling of the first sub-volume to cause the second sub-volume to flow its content to the second port, and (ii) in response to fluid pressure resulting from filling of the second sub-volume to cause the first sub-volume to flow its content to the first port.

2. The system according to claim 1, wherein the MCC arrangement functions as a periodic counter current (pcc) chromatography system including packed bed chromatography columns.

3. The system according to claim 1, wherein the chromatography columns are packed with media selected from the group consisting of: affinity chromatography media; ion exchange media; hydrophobic interaction chromatography media; reverse phase chromatography (RPC) media; and multi modal chromatography media.

4. The system according to claim 1, wherein the at least two containers are configured to hold the fluid output for a pre-determined period of time.

5. The system according to claim 1, wherein the virus inactivation means inactivates a virus by means of one or more of (1) pH changing, or UV irradiation; (2) the addition of one or more proteases and/or endoglycanases; (3) modification of the biomolecule by adding a chemical group; or (4) modification of the biomolecule by removing a chemical group.

6. The system according to claim 1, wherein the biomolecule is an antibody; and the first chromatography column is packed with Protein A media.

7. A virus inactivation device for a liquid chromatography system, comprising:
    an inlet port;
    an outlet port;
    a virus inactivation means;
    a group of containers, wherein each container in the group has a volume and a moveable sidewall arranged to divide the volume into a first sub-volume and a second sub-volume, wherein each container comprises a first port connected to the first sub-volume and a second port connected to the second sub-volume;

a fluid controller connected to the inlet port, to the outlet port and to the first port and to the second port of each container in the group, respectively;

wherein the fluid controller is configured to:
  select a container in the group that is empty or has been in a filled state during a time equal to or longer than a virus inactivation time,
  determine how much fluid should be directed to the selected container,
  direct the fluid flow from the inlet port to a first or second port of an empty sub-volume of the selected container in the group,
  determine when the sub-volume of the selected container is filled, and
  continuously inactivate the virus by successively directing the fluid flow to another empty sub-volume of another container in the group, which container is empty or has been in a filled state during a time equal to or longer than the virus inactivation time, whereby fluid pressure resulting from the filling of the empty sub-volume acts on the moveable side wall to cause the opposing filled sub-volume to flow its content to the outlet port, wherein the moveable sidewall of each container is movable (i) in response to fluid pressure resulting from filling of the first sub-volume to cause the second sub-volume to flow its content to the second port, and (ii) in response to fluid pressure resulting from filling of the second sub-volume to cause the first sub-volume to flow its content to the first port.

8. The virus inactivation device according to claim 7, wherein the virus inactivation means comprises:
  a pH lowering device arranged between the inlet port and the fluid controller; and
  a pH rising device arranged between the fluid controller and the outlet port.

9. The virus inactivation device according to claim 7, wherein the virus inactivation means is an UV light source.

10. The virus inactivation device according to claim 7, wherein the fluid controller is programmed to calculate the number of containers in the group to be at least N containers, wherein $N=T\times f/V+1$, where T is the predetermined virus inactivation time, and optionally including time for container washing and either pH raising and lowering, or UV exposure time, f is the inlet flow, and V is the volume of one container in the group of containers.

11. The virus inactivation device according to claim 7, wherein at least two containers are used in parallel.

12. The system according to claim 3, wherein the affinity chromatography media comprises Protein A media or Protein L media.

13. The system according to claim 5, wherein the chemical group comprises a polymer.

14. The system according to claim 5, wherein the chemical group comprises polyethylene glycol (PEG).

15. The system according to claim 6, wherein the antibody comprises a monoclonal antibody or a fusion antibody or fragment thereof.

* * * * *